United States Patent
Yoon et al.

(10) Patent No.: US 12,007,327 B2
(45) Date of Patent: Jun. 11, 2024

(54) OPTICAL BIO-SENSING DEVICE FOR BIO-MATERIAL ANALYSIS USING UPCONVERSION NANOPARTICLES, AND BIO-MATERIAL QUANTITATIVE ANALYSIS USING THE SAME

(71) Applicant: AJOU UNIVERSITY INDUSTRY-ACADEMIC COOPERATION FOUNDATION, Suwon-si (KR)

(72) Inventors: Hyun C Yoon, Seoul (KR); Ka Ram Kim, Suwon-si (KR); Hyeong Jin Chun, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 496 days.

(21) Appl. No.: 17/173,327

(22) Filed: Feb. 11, 2021

(65) Prior Publication Data

US 2021/0262935 A1 Aug. 26, 2021

(30) Foreign Application Priority Data

Feb. 21, 2020 (KR) .......................... 10-2020-0021669

(51) Int. Cl.
*C09K 11/77* (2006.01)
*C12Q 1/06* (2006.01)
*G01N 21/64* (2006.01)
*G02B 5/12* (2006.01)

(52) U.S. Cl.
CPC ...... *G01N 21/6428* (2013.01); *C09K 11/7773* (2013.01); *C12Q 1/06* (2013.01); *G01N 21/6402* (2013.01); *G01N 21/6456* (2013.01); *G02B 5/12* (2013.01); *G01N 2201/06113* (2013.01)

(58) Field of Classification Search
CPC .. G01N 21/6428; G01N 21/6456; C12Q 1/06; G02B 5/12; C09K 11/7773
See application file for complete search history.

(56) References Cited

FOREIGN PATENT DOCUMENTS

| KR | 10-2017-0075221 A | 7/2017 |
|---|---|---|
| KR | 10-2018-0112363 A | 10/2018 |

*Primary Examiner* — David W Berke-Schlessel
*Assistant Examiner* — Trent R Clarke
(74) *Attorney, Agent, or Firm* — Sughrue Mion, PLLC (57) ABSTRACT

An optical bio-sensing device includes a transparent substrate covering a top of a space accommodating therein a sample containing a target bio-material; a signal converter fixed to the transparent substrate, and including the upconversion nanoparticles for receiving incident light and emitting converted light of a wavelength shorter than a wavelength of the incident light; a signal reflector including retroreflection particles bindable to the signal converter via the target bio-material, wherein the retroreflection particles retroreflect the converted light; a light source for irradiating the incident light to the signal converter; and a light receiver for receiving light retroreflected from the signal reflector.

11 Claims, 11 Drawing Sheets

OPTICAL BIO-SENSING DEVICE FOR BIO-MATERIAL ANALYSIS USING UPCONVERSION NANOPARTICLES, AND BIO-MATERIAL QUANTITATIVE ANALYSIS USING THE SAME

CROSS-REFERENCE TO RELATED APPLICATION

This application claims a benefit under 35 U.S.C. § 119(a) of Korean Patent Application No. 10-2020-0021669 filed on Feb. 21, 2020, on the Korean Intellectual Property Office, the entire disclosure of which is incorporated herein by reference for all purposes.

BACKGROUND

1. Field

The present disclosure relates to an optical bio-sensing device capable of quantitative analysis of a bio-material in an optical manner using upconversion emission and retroreflection, and a bio-material quantitative analysis using the same.

2. Description of Related Art

Conventionally, in a method mainly used to perform optical quantitative/qualitative analysis of biological analytes including immunoassay and molecular diagnostics, detection of a signal intensity of a signal label causing fluorescence or emission is applied to a molecular-level reaction. This analysis method has been optimized in consideration of the signal intensity and stability based on a type of signal label. With development of new signal labels, optical analysis methods have also been developed. A type of the signal label may include organic compounds, metal complex compounds, and particles carrying the same thereon, quantum dots, GFP (green fluorescent protein), etc. The signal labels are used in various ways according to requirements of each analysis target based on the intensity, stability, duration, and type of emission spectrum thereof.

One of the new signal labels is an upconversion nanoparticle (UCNP) which may generate a signal by inducing a bottom-up energy conversion (upconversion) as opposed to a top-down energy conversion (downconversion) as shown in fluorescence. Therefore, in the UCNP may use excitation light of near-infrared (NIR) which is transmissive, prevent autofluorescencing, and suppresses photo-induced degradation and photobleaching of an analysis target material, without using excitation light of a visible or ultraviolet region commonly used in fluorescence. Based on these advantages, the UCNP may exclude factors that hinder signal sensitivity that organic compound-based signal labels may have. However, in general, in order to observe upconversion emission, a complex optical system design and expensive components are required. Further, a miniaturized analysis optical system to satisfy demand for on-site diagnosis analysis such as diagnostic tests is currently being studied in the art.

Fluorescence analyzers are widely used to diversify target materials and improve analytical sensitivity for immunoassay and molecular diagnosis as required in the current diagnostic test market, but have following problems.

First, a fluorescent dye widely used as an optical probe for immunoassay may provide a valid signal only when using excitation light at a specific wavelength. Thus, the fluorescent dye requires a combination of a halogen lamp that provides light of all wavelengths as a light source and a monochromator (or excitation filter) that may select and irradiate light of a specific wavelength from all wavelengths of light from the halogen lamp. This may cause the optical equipment to be larger. In order to observe various emission wavelengths, a variety of excitation lights are required. Thus, the fluorescent dye has a limit in terms of commercialization for a diagnostic test equipment for miniaturization. This may be solved by using a short wavelength laser diode.

The fluorescent dye which is excited by light from the light source and emits light of an emission wavelength under fluorescence is stable. However, quenching due to water molecules and other electron transfer materials that are continuously exposed thereto during reaction, self-quenching between fluorescent materials, as well as photobleaching due to excitation light having a certain intensity or greater may be induced. Selection of fluorescent materials for stable signal detection requires a lot of trial and error. Therefore, the fluorescent signal label based on an organic/inorganic molecular group should be subjected to optimization for optical equipment specifications, including optical filtering based on specified excitation light and emission wavelength, and due to light leakage.

In addition, use of most of organic/inorganic fluorescent molecular groups is avoided in image detection of biological tissues such as cells. This is because, in most cases, the excitation light wavelength of the molecular group is close to 400 nm, and the excitation wavelength passing through the cell is in an ultraviolet region that may cause denaturation and destruction of proteins including genetic materials (DNA and RNA) inside nucleus. Thus, it is difficult to obtain research results on living cell activity using the organic/inorganic fluorescent molecular groups unless activity of cells is intended to be chemically fixed.

A first example of the conventional fluorescence based optical cytometry techniques having the above described limitations includes an observation method using a green fluorescence protein or luciferase in a cell. In order to express the green fluorescence protein or luciferase in cells, a viral vector is transfected thereto to add a factor that may actually affect activity of the cell itself. A second example thereof employs quantum dots. In this case, an intracellular environment may lower quantum efficiency, and cytotoxicity may be caused due to heavy metals constituting the quantum dot. A third example thereof includes a method of observing cell growth and activity by introducing magnetic nanoparticles into cells to obtain magnetic resonance images. However, a current resolution of magnetic resonance imaging remains within 1 to 3 $mm^2$, which is suitable for observation at a tissue level rather than at a cell level, but has limitations in observation of individual cells of several tens of micrometers.

In order to detect a fluorescence signal from the fluorescent dyes, the irradiated excitation light and the fluorescent signal induced from the fluorescent dye in response thereto should be separated from each other. Therefore, a separate emission filter is essential. Further, for sensitive detection of the fluorescent signal, an expensive light-receiving device such as a photomultiplier tube (PMT) is essential. In addition, very precise arrangement and assembly between these optical components are required. These act as limiting factors in implementation of devices for purpose of miniaturization of an optical bio-sensor and the field diagnosis.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

One purpose of the present disclosure is to provide an optical bio-sensing device that uses wavelength-selective reflection ability of retroreflection particles that may selectively obtain only upconversion emission, while minimizing interference of near-infrared light as excitation light required for upconversion emission.

Another purpose of the present disclosure is to provide a method of performing a quantitative analysis on presence or absence of a bio-material, concentration, etc. thereof using the optical bio-sensing device.

Purposes of the present disclosure are not limited to the above-mentioned purpose. Other purposes and advantages of the present disclosure as not mentioned above may be understood from following descriptions and more clearly understood from embodiments of the present disclosure. Further, it will be readily appreciated that the purposes and advantages of the present disclosure may be realized by features and combinations thereof as disclosed in the claims.

One aspect of the present disclosure provides an optical bio-sensing device for bio-material analysis using upconversion nanoparticles, the bio-sensor comprising: a transparent substrate covering a top of a space accommodating therein a sample containing a target bio-material; a signal converter fixed to the transparent substrate, and including the upconversion nanoparticles for receiving incident light and emitting converted light of a wavelength shorter than a wavelength of the incident light; a signal reflector including retroreflection particles bindable to the signal converter via the target bio-material, wherein the retroreflection particles retroreflect the converted light; a light source for irradiating the incident light to the signal converter; and a light receiver for receiving light retroreflected from the signal reflector.

In one implementation of the optical bio-sensing device, the signal converter includes the upconversion nanoparticles chemically binding to a bottom face of the transparent substrate.

In one implementation of the optical bio-sensing device, the signal converter includes a transparent polymer film formed on a bottom face of the transparent substrate, wherein the upconversion nanoparticles are dispersed in the transparent polymer film.

In one implementation of the optical bio-sensing device, each of the upconversion nanoparticles is made of a compound represented by a following Chemical Formula 1 and doped with a lanthanide element:

$NaYREF_4$ <Chemical Formula 1> wherein in the Chemical Formula 1, RE represents one selected from a group consisting of Yb, Er, Tm, Gd, Mn, Lu, Ce and Nd.

In one implementation of the optical bio-sensing device, each of the retroreflection particles includes a first bio-recognition material capable of selectively binding to the target bio-material, wherein the signal converter includes a second bio-recognition material capable of selectively binding to the target bio-material.

In one implementation of the optical bio-sensing device, when the incident light having a wavelength of an infrared region is irradiated onto the upconversion nanoparticles, the upconversion nanoparticles convert the incident light to the converted light having a wavelength of a visible region, and emit the converted light, wherein the retroreflection particles retroreflect the converted light.

In one implementation of the optical bio-sensing device, a size of each of the retroreflection particles is smaller than a wavelength of the incident light and is larger than a wavelength of the converted light.

Another aspect of the present disclosure provides a method for quantitative analysis of a bio-material using the optical bio-sensing device as defined above, the method comprising: a first step of reacting the retroreflection particles with a detection target solution containing the target bio-material; a second step of selectively binding the signal reflector having the target bio-material binding thereto to the signal converter; a third step of irradiating the incident light of an infrared wavelength region to the signal converter; a fourth step of retroreflecting the converted light of a visible wavelength region from the signal converter using the retroreflection particles; and a fifth step of generating and analyzing an image of the retroreflected light.

In one implementation of the method, a size of each of the retroreflection particles is smaller than a wavelength of the incident light and is larger than a wavelength of the converted light, such that the incident light is scattered from the retroreflection particles, and the converted light is retroreflected from the retroreflection particles.

In one implementation of the method, the method further comprises, after the second step and before the third step, removing the signal reflector that does not bind to the signal converter.

In one implementation of the method, the fifth step includes counting a number of signals of the signal reflector based on the generated image, and quantitatively analyzing a concentration of the target material, based on the counted number.

According to the present disclosure, the bio-sensing device may selectively reflect the signal while the initial incident light and the upconversion emission are separated from each other using the retroreflection particles and the upconversion nanoparticles. Thus, the device having a relatively simple configuration may analyze the target bio-material without use of the conventional sophisticated configuration and expensive optical equipment. The miniaturization of the biosensing device may be achieved.

Further, the light emitted from the upconversion nanoparticles inhibits the denaturation and destruction of the target bio-material. Thus, the present device may be applied to studies on the activity of living cells.

In addition to the effects as described above, specific effects of the present disclosure will be described together with the detailed description for carrying out the disclosure.

DETAILED DESCRIPTIONS

For simplicity and clarity of illustration, elements in the figures are not necessarily drawn to scale. The same reference numbers in different figures denote the same or similar elements, and as such perform similar functionality. Moreover, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
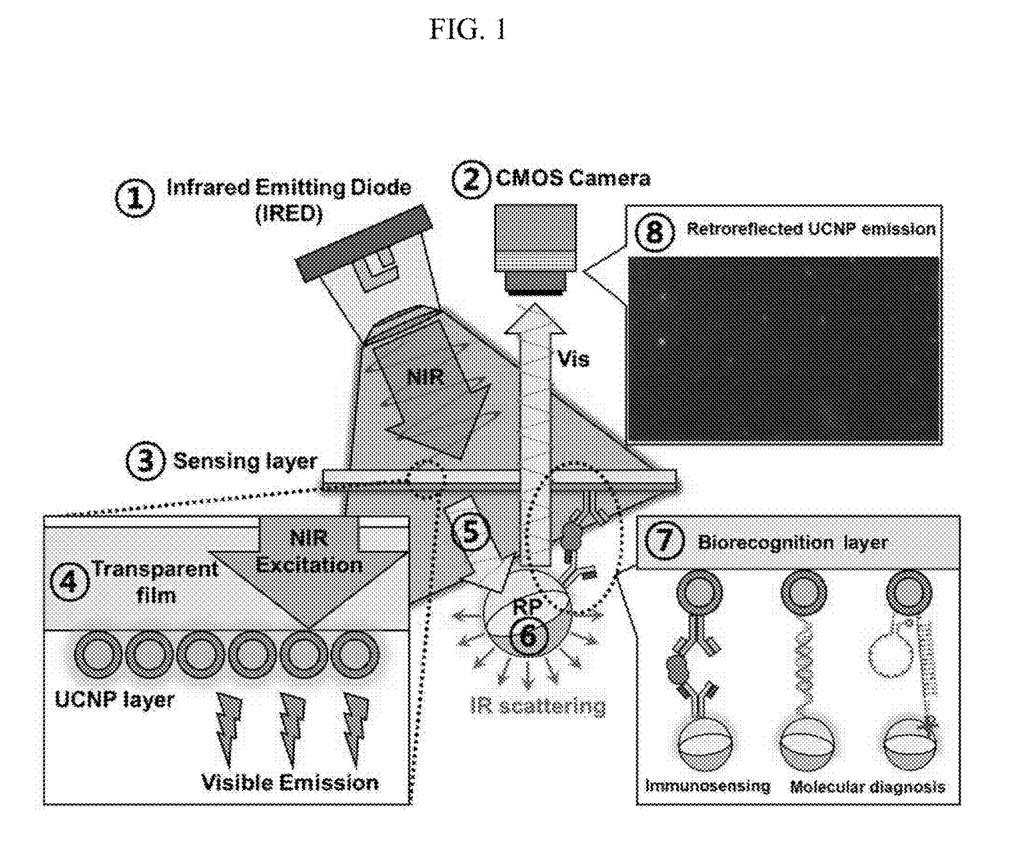
FIG. 1 is a schematic diagram to illustrate an optical bio-sensing device for bio-material analysis using upconversion nanoparticles according to the present disclosure.
Figure 2:
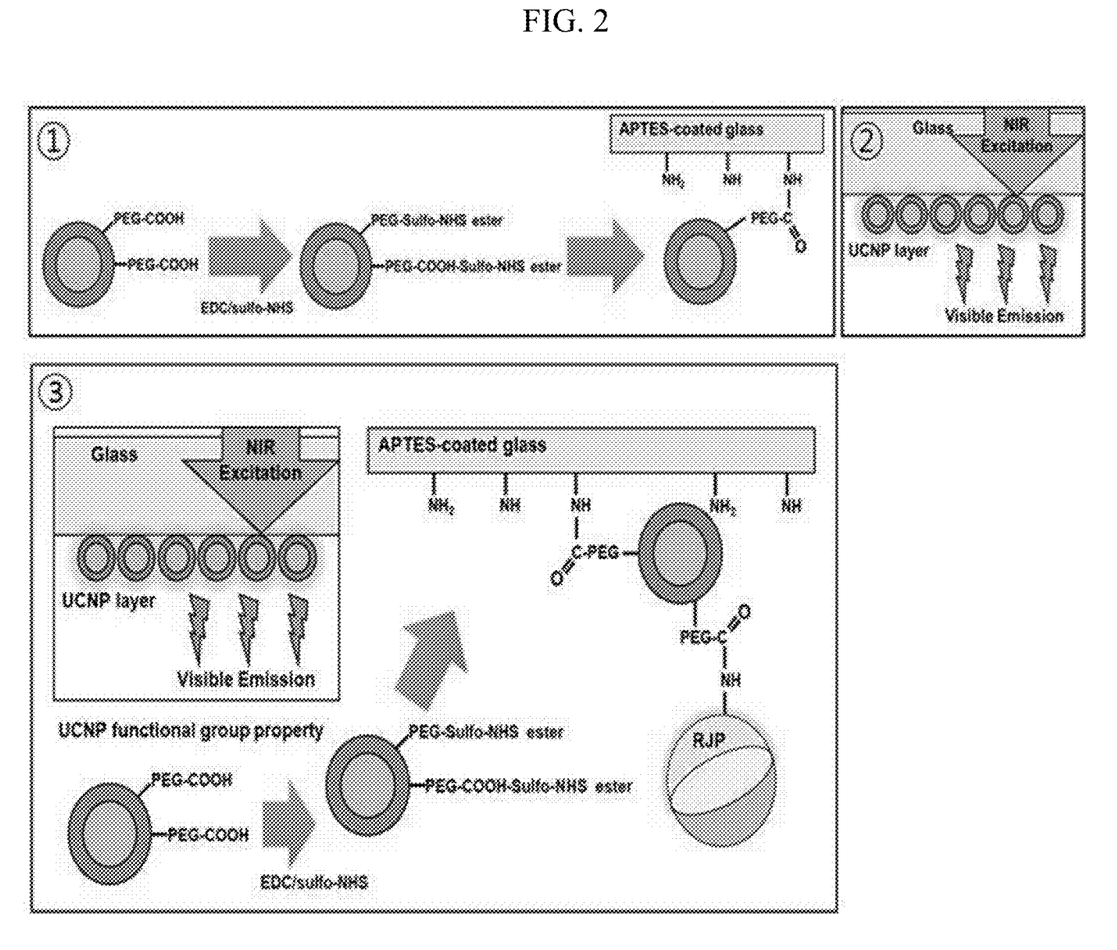
FIG. 2 is a schematic diagram for illustrating an embodiment of a signal converter fixed to a transparent substrate of the optical bio-sensing device shown in FIG. 1. ① in FIG. 2 is a schematic diagram showing a combination of a transparent substrate and a signal converter in accordance with an embodiment of the present disclosure. Specifically, ① in FIG. 2 indicates that the transparent substrate and the upconversion nanoparticles may be bonded to each other via a functional group introduced to the upconversion nanoparticles. ② in FIG. 2 is a diagram for illustrating a signal conversion process of the signal converter fixed to the transparent substrate when light of infrared wavelength is irradiated thereto according to an embodiment of the present disclosure. ③ of FIG. 2 is a schematic diagram showing a combination of the signal converter and retroreflection particles according to an embodiment of the present disclosure.
Figure 3:
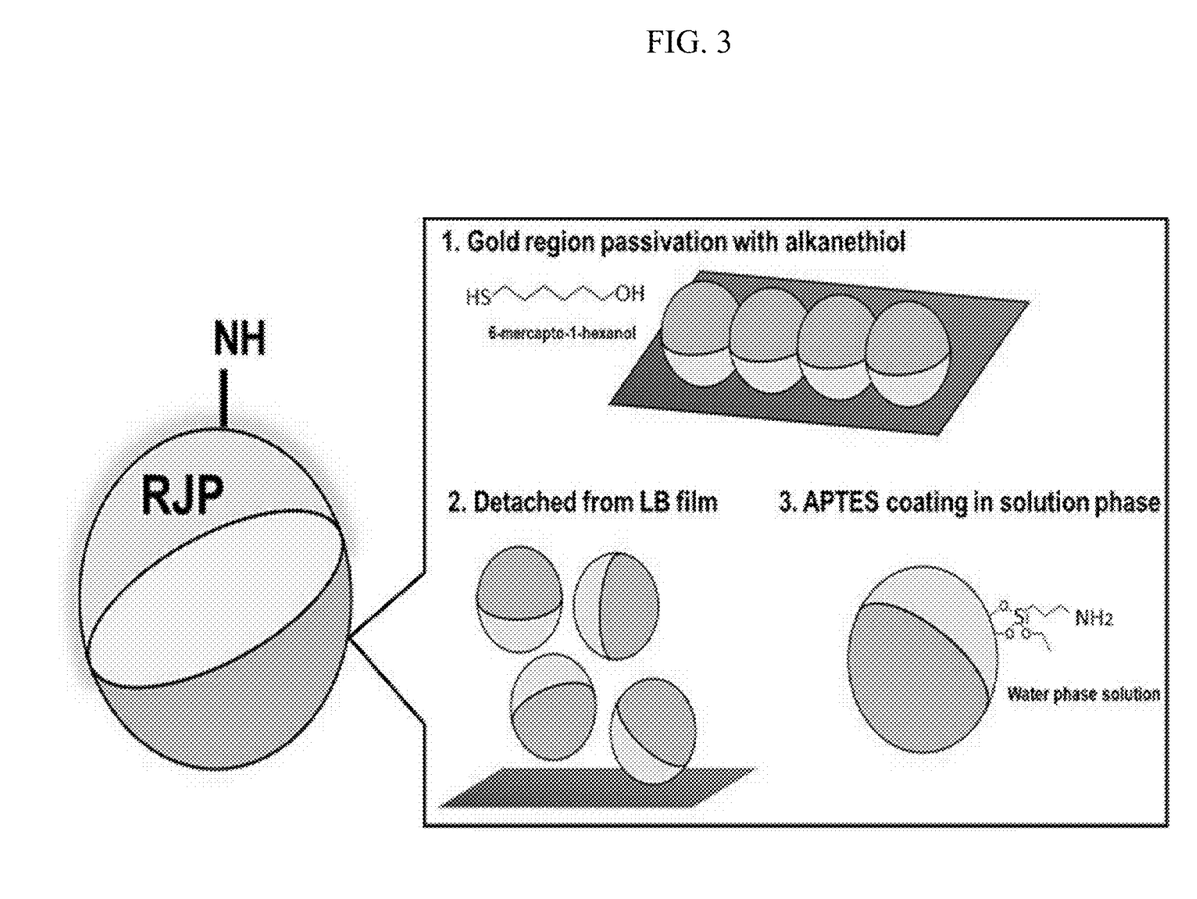
FIG. 3 is a schematic diagram for illustrating an embodiment of the retroreflection particles of the optical bio-sensing device shown in FIG. 1.
Figure 4:
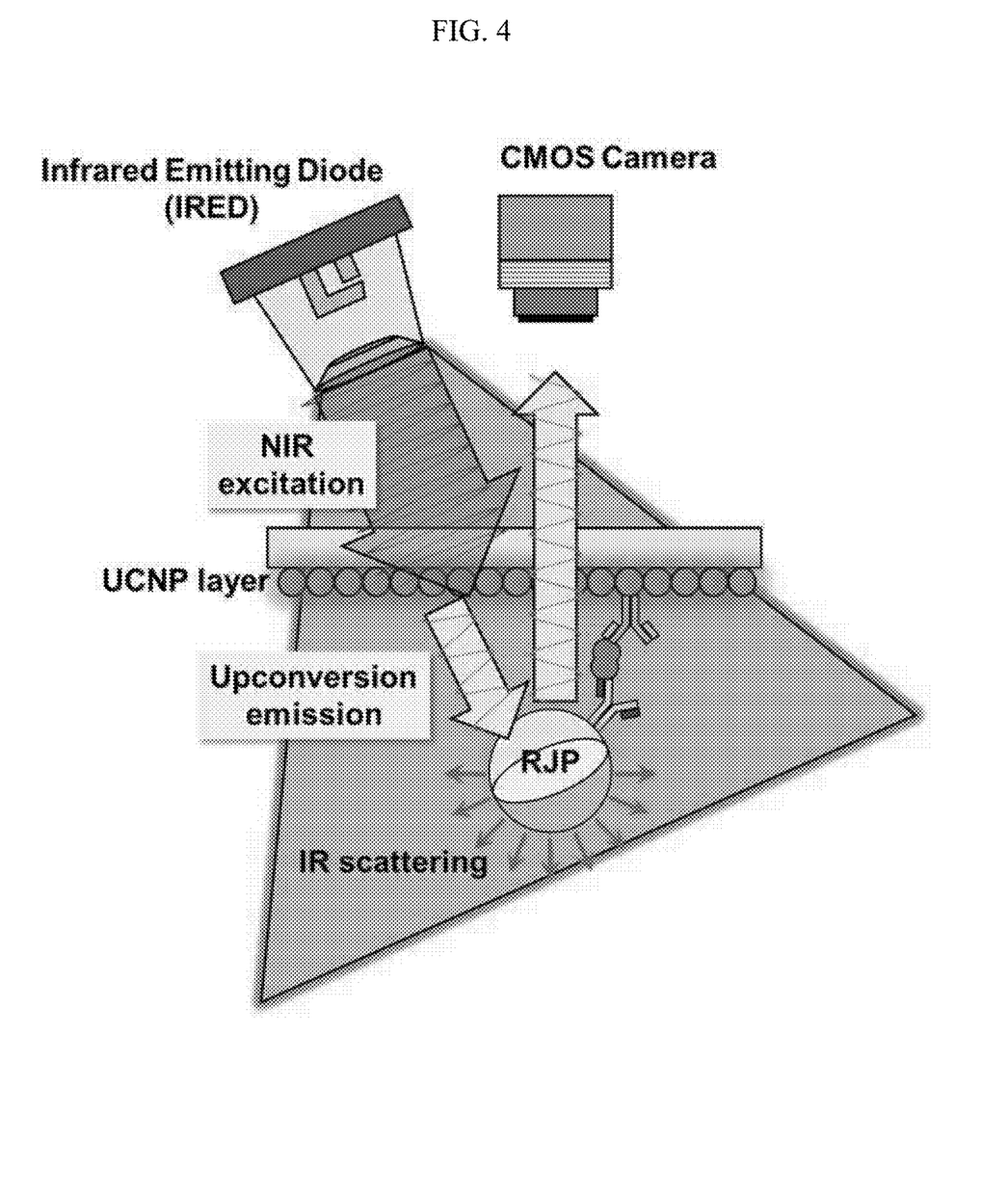
FIG. 4 is a schematic diagram for illustrating emission signal acquisition of the optical bio-sensing device shown in FIG. 1.
Figure 5:
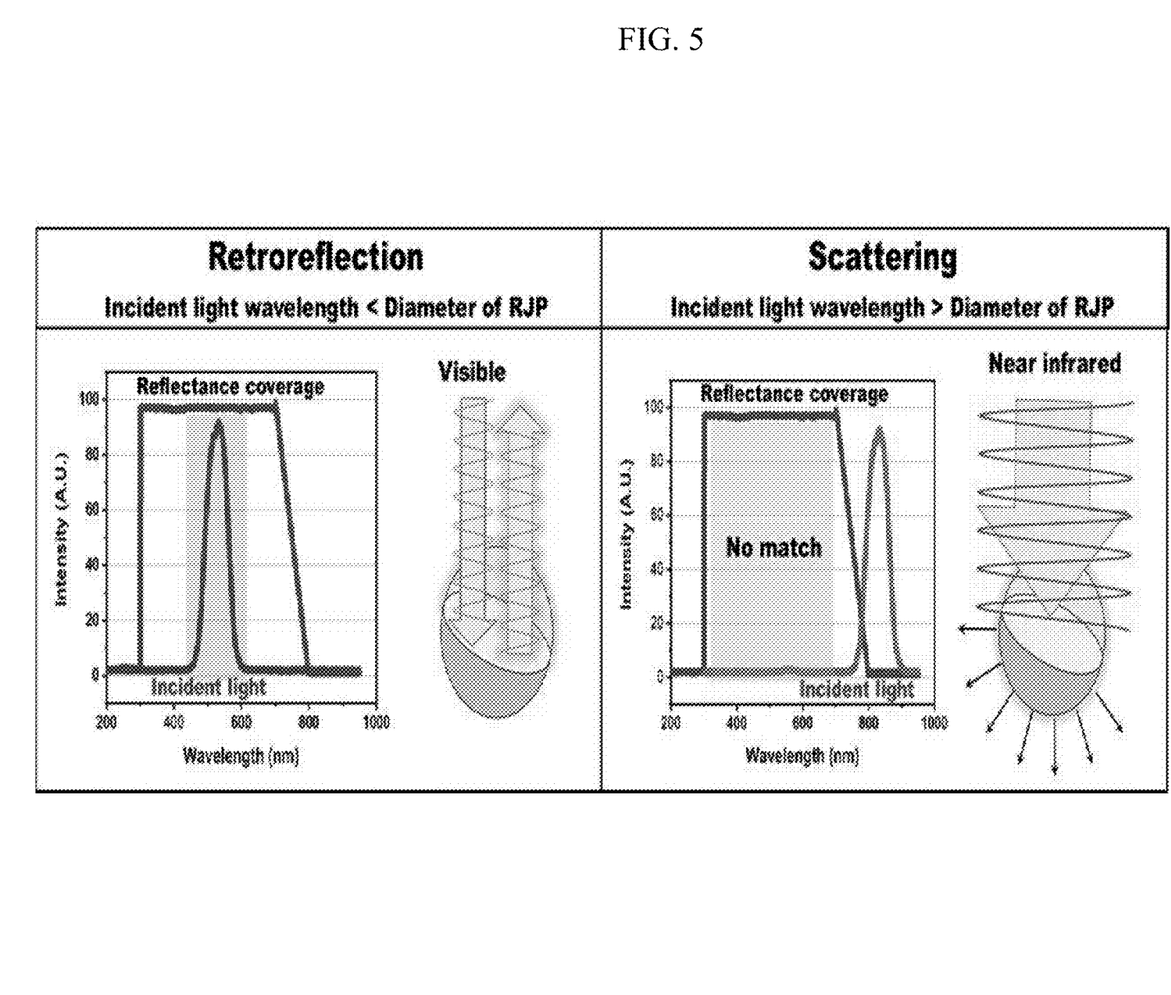
FIG. 5 is a schematic diagram to illustrate retroreflection performance of the retroreflection particles based on a wavelength band.

FIG. 1 is a schematic diagram to illustrate an optical bio-sensing device for bio-material analysis using upconversion nanoparticles according to the present disclosure. FIG. 2 is a schematic diagram for illustrating an embodiment of a signal converter fixed to a transparent substrate of the optical bio-sensing device shown in FIG. 1. ① in FIG. 2 is a schematic diagram showing a combination of a transparent substrate and a signal converter in accordance with an embodiment of the present disclosure. Specifically, ① in FIG. 2 indicates that the transparent substrate and the upconversion nanoparticles may be bonded to each other via a functional group introduced to the upconversion nanoparticles. ② in FIG. 2 is a diagram for illustrating a signal conversion process of the signal converter fixed to the transparent substrate when light of infrared wavelength is irradiated thereto according to an embodiment of the present disclosure. ③ of FIG. 2 is a schematic diagram showing a combination of the signal converter and retroreflection particles according to an embodiment of the present disclosure. FIG. 3 is a schematic diagram for illustrating an embodiment of the retroreflection particles of the optical bio-sensing device shown in FIG. 1. FIG. 4 is a schematic diagram for illustrating emission signal acquisition of the optical bio-sensing device shown in FIG. 1. FIG. 5 is a schematic diagram to illustrate retroreflection performance of the retroreflection particles based on a wavelength band.

Referring to FIG. 1 to FIG. 4, an optical bio-sensing device for bio-material analysis using upconversion nanoparticles according to the present disclosure includes a transparent substrate covering a top of a space accommodating therein a sample containing a target bio-material, a signal converter having upconversion nanoparticles fixed to the transparent substrate and receiving incident light and then emitting converted light of a wavelength shorter than a wavelength of the incident light, a signal reflector having retroreflection particles bindable to the signal converter via the target bio-material and retroreflecting the converted light, a light source for irradiating the incident light to the signal converter, and a light receiver for receiving light retroreflected from the signal reflector.

The transparent substrate may be made of a material through which incident light irradiated from a light source primarily transmits, and having excellent light transmittance. For example, the transparent substrate may be made of one material selected from glass, poly(methylmethacrylate), polystyrene, polycarbonate, and the like.

In an embodiment of the present disclosure, as shown in FIG. 2, the signal converter may include the upconversion nanoparticles chemically bonded to a bottom face of the transparent substrate. In this connection, in order to bind the upconversion nanoparticles to the bottom face of the transparent substrate, a functional group forming a covalent bond with the upconversion nanoparticles may be introduced on the bottom face of the transparent substrate. For example, when the transparent substrate is made of a polymer, the transparent substrate is subjected to a atmospheric pressure plasma treatment to impart a functional group to the surface of the transparent substrate so that functional groups present in a polymer chain are expressed thereon. When the transparent substrate is made of glass, a functional group may be introduced on the surface of the transparent substrate via silanization treatment. For example, when the transparent substrate is made of polymethylmethacrylate, carboxylation of a carboxylate ester group of the polymethylmethacrylate, and then a sequential silane reaction may allow an amine group to be exposed. In addition, a functional group may be introduced into the surface of the upconversion nanoparticles to be combined with the transparent substrate. For example, a carboxyl functional group may be introduced on the surface of the upconversion nanoparticles.

In one example, bonding between the upconversion nanoparticles having a carboxyl functional group on the surface thereof and the transparent substrate made of glass and subjected to the silanization process using aminosilane may be achieved via covalent bonds using 1-ethyl-3-(3-dimethylaminopropyl)carbodiimide hydrochloride (EDC)/N-hydroxysulfosuccinimide (sulfo-NHS) coupling reaction.

In one embodiment, the signal converter may include a transparent polymer film which is formed on a bottom face of the transparent substrate and in which the upconversion nanoparticles are dispersed.

The polymer film may include a transparent polymer material and the upconversion nanoparticles. The transparent polymer material is not particularly limited as long as it may transmit the light therethrough.

The upconversion nanoparticles may generate signals by inducing upconversion as opposed to downconversion. For example, when irradiating the upconversion nanoparticles with light in an infrared region corresponding to a long wavelength, the upconversion nanoparticles may exhibit emission of a visible region corresponding to a short wavelength.

In one embodiment, each of the upconversion nanoparticles may be made of a compound represented by a following Chemical Formula 1 and doped with a lanthanide element.

$NaYREF_4$  <Chemical Formula 1>

In the Chemical Formula 1, RE represents one selected from a group consisting of Yb, Er, Tm, Gd, Mn, Lu, Ce, and Nd.

The compound constituting the upconversion nanoparticle may be doped with neodymium (Nd) or ytterbium (Yb) ions as a sensitizer capable of absorbing infrared energy. Further, erbium (Er) or thulium (Tm) ions as an emission-inducing activator may be doped thereto. Emission wavelength energy based on the quantum efficiency may be determined according to a configuration of the pair of the sensitizer and the activator.

In one example, the retroreflection particles may have retroreflection capability, and may react selectively with the target bio-material and may direct the converted light to the light receiver, and at the same time, may induce scattering and reflection phenomena, based on the incident light wavelength.

In one embodiment, each of the retroreflection particles may include a transparent core particle and a total reflection coating layer covering a portion of a surface of the core particle.

The core particle may have a spherical shape. In the present disclosure, the term 'spherical' is defined to include not only a perfect sphere with the same radii from a center to all points on a surface thereof, but also a substantial sphere with a difference of smaller than about 10% between maximum and minimum radii.

Further, the core particle may be made of a transparent material capable of transmitting light therethrough. For example, the core particle may be made of a transparent oxide or a transparent polymer material. The transparent oxide may include silica, glass. etc. However, the disclosure is not limited thereto. The transparent polymer material may include, for example, polystyrene, and poly(methylmethacrylate).

The total reflection coating layer may retroreflect at least a portion of light traveling inside the core particle toward the light receiver, and may be made of a high reflectivity material. For example, the total reflection coating layer may be made of one selected from aluminum (Al), chromium (Cr), copper (Cu), zinc (Zn), silver (Ag), gold (Ag), and the like.

In one embodiment, the retroreflection particles may include a first bio-recognition material that may selectively bind to the target material. The signal converter may include a second bio-recognition material that may selectively bind to the target material.

The bio-recognition material may be made of a material that may selectively bind to the target bio-material. In the present disclosure, the bio-recognition material may vary depending on the target bio-material to be detected. For example, the bio-recognition material may be a material such as protein, nucleic acid, and ligand.

The first bio-recognition material may be directly or indirectly bonded to a portion of a surface of the core particle free of the total reflection coating layer of the retroreflection particle, as shown in FIG. 3. In one embodiment, the first bio-recognition material may be modified only on the exposed surface of the core particle, and may not be modified on a surface of the total reflection coating layer. For example, in a process of preparing the retroreflection particles, first, a bio-recognition material modification prevention material such as a compound including 6-mercapto-1-hexanol, 2-mercaptoethanol, 3-mercapto-propanol, 4-mercapto-1-butanol, PEG (polyethylene glycol) and an alkane-based spacer may be modified on the surface of the total reflection coating layer to perform passivation, and then the first bio-recognition material may react with the core particle, such that the first bio-recognition material may be modified only on the exposed surface of the core particle. In this connection, before performing the process of modifying the first bio-recognition material on the exposed surface of the core particles, a process of introducing a function group may be performed using a compound such as a silane compound to facilitate the modification of the first bio-recognition material. In this way, when the first bio-recognition material is selectively modified only on the exposed surface of the core particles, the exposed surface of the core particles may be oriented toward the light receiver, such that a stronger retroreflection signal may be induced, thereby improving the sensitivity of the biosensor.

In one embodiment, as shown in FIG. 4, when the incident light having a wavelength of an infrared region is irradiated to the upconversion nanoparticles, the upconversion nanoparticles convert the wavelength of the incident light to emit the converted light having a wavelength of a visible region, and the retroreflection particles may retroreflect the converted light.

In one embodiment, as shown in FIG. 5, the size of each of the retroreflection particles may be smaller than the wavelength of the incident light and larger than the wavelength of the converted light. The retroreflection particles may have retroreflection capability of light having a wavelength smaller than the size of the retroreflection particle.

When the size of each of the retroreflection particles is smaller than the wavelength of light irradiated to the retroreflection particles, the retroreflection ability may be enabled to retroreflect the light. To the contrary, when the size of each of the retroreflection particles is larger than the wavelength of light irradiated to the retroreflection particles, scattering, dissipation, or diffraction of the light may be induced, resulting in a problem that the retroreflection effect is deteriorated. In one embodiment, when the incident light is infrared light and the converted light is visible light, the size of each of the retroreflection particles may be in a range of about 1 μm to about 800 nm.

The light source is disposed on the transparent substrate such that the incident light may be irradiated from the light source to the signal converter. Light from the light source may have a wavelength larger than the size of each of the retroreflection particles. Preferably, the light from the light source may be light in an infrared region. Specifically, the light from the light source may be a near-infrared laser or the like.

The light receiver is disposed above the transparent substrate and is spaced apart from the light source. The light receive is configured to receive the light retroreflected from the signal reflector, and to quantitatively analyze information on presence or absence of the target bio-material, concentration, etc. thereof. The configuration of the light receiver is not particularly limited as long as the light receiver receives the retroreflected light and analyzes information on the target material. In one embodiment, the light receiver may include an imaging unit that images the retroreflected optical signal and an image analyzer that analyzes image information generated by the imaging unit. The imaging unit may include a known image generating device such as a CMOS camera with a zoom lens. However, the disclosure is not particularly limited thereto. The image analyzer may include a known image analysis system without limitation.

In one embodiment, the light receiver may quantitatively analyze the concentration of the target bio-material by the image analyzer counting the number of signals of the signal reflector from the image generated by the imaging unit.

Hereinafter, a method of quantitative analysis of the target bio-material using the optical bio-sensing device as described with reference to FIG. 1 to FIG. 5 will be described in detail. A method of quantitatively analyzing a target bio-material according to an embodiment of the present disclosure may be performed using the optical bio-sensing device according to the present disclosure.

Referring to FIG. 1 to FIG. 5, the method of quantitative analysis of the target bio-material according to the present disclosure may include a first step of reacting the retroreflection particles with a detection target solution containing the target bio-material, a second step of selectively coupling the signal reflector having the target bio-material coupled thereto to the signal converter, a third step of irradiating incident light of an infrared region to the signal converter, a fourth step of retroreflecting converted light of a visible light wavelength converted by the signal converter using the retroreflection particles, and a fifth step of generating and analyzing an image of the retroreflected light.

In the first step, as described above, the retroreflection particles may have the first bio-recognition material, and thus may selectively bind to the target bio-material.

In the second step, the signal reflector having the target bio-material coupled thereto may react with the signal converter such that the signal reflector to which the target bio-material is coupled may be selectively coupled to the signal converter. In this case, the selective reaction occurs between the second bio-recognition material modified on the signal reflector and the target bio-material bonded to the signal reflector. That is, the retroreflection particles of the signal reflector reacted with the target bio-material may be fixed to the transparent substrate via the target bio-material, while the retroreflection particles that have not reacted with the target bio-material may not be fixed to the transparent substrate.

In an embodiment, a step of removing the signal reflector not coupled to the signal converter may be further included after the second step and before the third step.

In the third step, when irradiating light to the signal converter through the transparent substrate, the upconversion nanoparticles of the signal converter fixed to the transparent substrate may be fixedly disposed at a position adjacent to the transparent substrate to which light is incident and may receive the incident light to emit the converted light. The retroreflection particles coupled to the signal converter via the target bio-material may strongly retroreflect the converted light.

Further, since the first bio-recognition material is modified only on the exposed surface of the core particle of the retroreflection particle, the exposed surfaces of the core particles of the retroreflection particles fixed onto the transparent substrate and coupled to the signal converter via the target bio-material may be oriented towards the transparent substrate.

The fifth step may quantitatively analyze the concentration of the target material by counting the number of signals of the signal reflector from the generated image. For example, light retroreflected from the retroreflection particles appears as dots on the generated image. Thus, the concentration of the target bio-material may be quantitatively analyzed by counting the number of the retroreflection particles based on the dots on the image.

In one embodiment, in order to increase an analysis area of the target bio-material, in the fifth step, a plurality of consecutive captured images may be generated while moving the irradiation area of the incident light in a single direction for a preset time duration in a time-lapse manner. Then, the generated images may be collected and then the collected images may be subjected to an image processing process to present a single image, which may in turn be analyzed. Thus, the presence or absence and the concentration of the target bio-material may be quantitatively analyzed.

According to the optical bio-sensing device according to the present disclosure and the bio-material analysis method using the same, simpler and smaller bio-sensor based analysis than the conventional optical bio-sensing device may be achieved. Further, tissues and organs composed of cells as well as other bio-materials including blood and urine may be analyzed. That is, the analysis may be effectively performed in an environment in which elements constituting the target biomaterial are various or transmission of the excitation light is inhibited due to a thickness of a cell layer constituting the target biomaterial.

Example 1

① Preparation of Transparent Substrate Made of Glass

The preparation process of the transparent substrate made of glass is as follows. First, the glass substrate was subjected to an ultrasonic wave based washing process using isopropyl alcohol and ethyl alcohol as solvents to remove impurities that may exist on a surface of the glass substrate. Then, a silanization reaction was performed on the glass substrate for 4 hours using 3-aminopropyltriethoxysilane (APTES) aqueous solution having a concentration of 1 to 10%. Then, the glass substrate subjected to the silanization reaction was heated to 40° C. or higher within 1 hour, was washed with distilled water, and was dried to prepare the glass transparent substrate in which amino silane was bonded to a surface thereof. The amino silane may be used as a functional group in immobilization of the signal converter to the transparent substrate.

② Preparation of Transparent Substrate Made of Polymer

In the preparation of a transparent substrate made of a polymethyl methacrylate (PMMA), first, the PMMA substrate was subjected to atmospheric plasma treatment for 30 to 60 seconds to convert a carboxylate ester functional group as a residue exposed on the PMMA surface into a carboxyl functional group. Then, a pH 11 carbonate buffer solution was introduced into a reaction solution in which 0.1 to 1% APTES was dissolved in a carbonate buffer. Reaction occurred for up to 4 hours to prepare the PMMA substrate having an exposed amine functional group at an end thereof. The amine group may serve as a functional group capable of inducing a covalent bond to a bio-recognition molecule which is formed later.

③ Preparation of Retroreflection Particles

First, The total reflection coating layer of each of the retroreflection particles was made of gold. A gold surface reacted with a mixed solution of dimethylsulfoxide (DMSO) and 6-mercapto-1-hexanol having a concentration of 10 to 50 mM for at least 6 hours, and then, washing and solvent conversion were performed using DMSO, ethanol, distilled water, and phosphate buffered saline sequentially. Then, the particles were dispersed in 10 mg/mL aqueous solution based on APTES and were mixed in dark condition at room temperature and reaction occurred for at least 1 hour, thereby to prepare retroreflection particles onto which an amine functional group was introduced. Later, a crosslinker such as glutaraldehyde and bis(sulfosuccinimidyl)suberate (BS3) may be additionally introduced. Thus, the first bio-recognition material may be modified.

Experimental Example A: Retroreflection Analysis of Retroreflection Particles Based on Wavelength Region In order to verify scattering/dissipation effect of the retroreflection particles based on the wavelength region, retroreflection ability of the retroreflection particles was identified using a white light source and a near-infrared light source. First, the retroreflection particles were immobilized on a surface of the glass substrate. The glass substrate was irradiated with each of white light and 980 nm infrared light to identify whether a signal was detected. The results are shown in FIG. 6.

Figure 6:
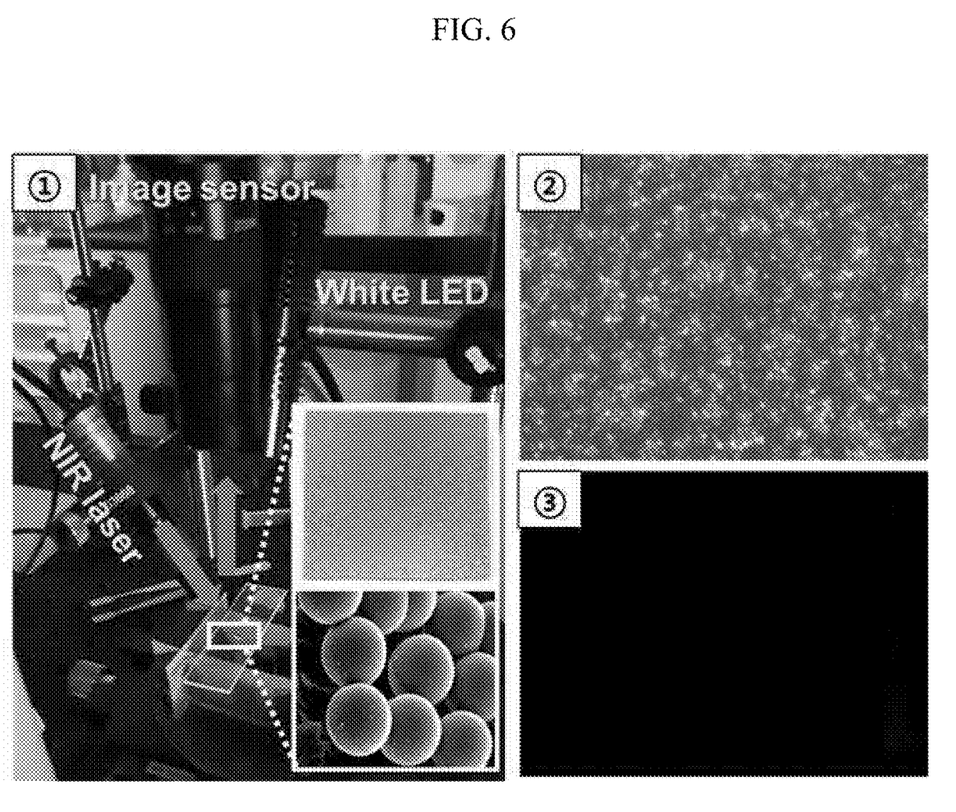
FIG. 6 is a diagram showing a retroreflection analysis result of the retroreflection particles based on a wavelength region in Experimental Example A of the present disclosure. ① in FIG. 6 is a diagram showing a process for performing Experimental Example A, and is an image showing an optical system for retroreflection measurement having a white light source and laser light source installed therein, and a transparent substrate on which the retroreflection particles are immobilized. ② in FIG. 6 is an image obtained through a CMOS camera when white light is irradiated. ③ in FIG. 6 is an image obtained through a CMOS camera when (near-)infrared laser is irradiated.

Referring to FIG. 6, on an image obtained by irradiating the white light onto the retroreflection particles, bright spots appear. On an image obtained by irradiating the retroreflection particles with the infrared light, the bright spots do not appear. Thus, when the retroreflection particles are irradiated with the white light having a wavelength of the visible region, a retroreflection signal is obtained. However, when the near-infrared light having a wavelength larger than a diameter of each of the retroreflection particles is irritated to the retroreflection particles, the scattering and dissipation occur on the retroreflection particles, so that the image sensor cannot obtain a signal. In other words, according to the present disclosure, the incident light of the infrared region may pass through the transparent substrate and excite upconversion nanoparticles. The excitation light may be scattered or dissipated on the retroreflection particle having a size smaller than the infrared wavelength, so that the interference of the excitation light is excluded from a retroreflection based optical system. At the same time, the upconversion nanoparticles may receive the incident light and emit the converted light of the visible region. Then, the retroreflection particles may retroreflect the converted light of the visible region. Thus, the retroflected light may be obtained as the dots by the light receiver. Thus, signal quantification may be achieved via counting of the number of the dots.

Experimental Example B: Characterization of Upconversion Nanoparticles

To characterize the upconversion nanoparticles according to the present disclosure, upconversion nanoparticles of 35 nm made of $NaYREF_4$ having emission of yellowish green (545, 660 nm) (where RE is Yb, Er, Tm, Gd, Mn, or Lu) were prepared. A silica shell was formed on surfaces of the prepared upconversion nanoparticles. Thus, the upconversion nanoparticles having the silica shell formed thereon were prepared. To analyze a morphology of the prepared upconversion nanoparticles, an image thereof was obtained using a scanning electron microscope (SEM). In order to examine the emission of the prepared upconversion nanoparticles, the upconversion nanoparticles were irradiated with light to identify the emission of the upconversion nanoparticles. The results are shown in FIG. 7.

Figure 7:
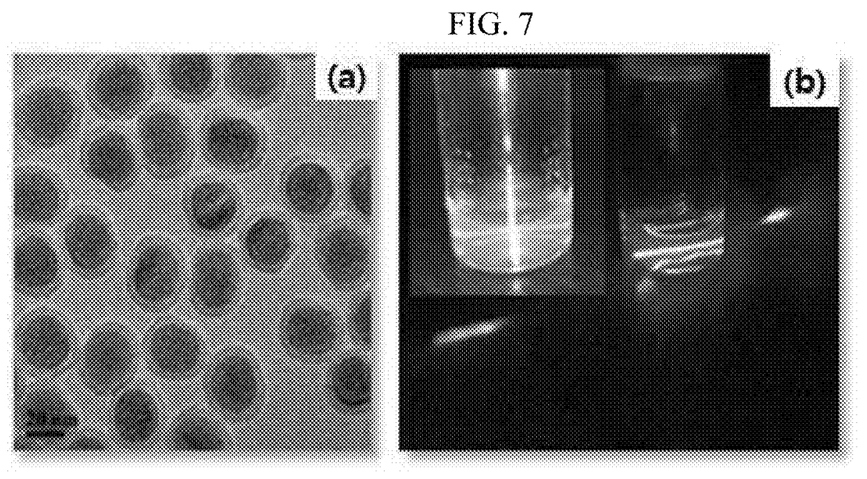
FIG. 7 is a diagram showing a result of analyzing properties of upconversion nanoparticles in Experimental Example B of the present disclosure. (a) in FIG. 7 is an SEM image showing a shape of upconversion nanoparticles. (b) in FIG. 7 is an image showing emission of upconversion nanoparticles.

Referring to FIG. 7, it may be seen that the silica shell was formed on the upconversion nanoparticles in (a). In (b), it may be seen that the upconversion nanoparticles may emit light irradiated to the upconversion nanoparticles.

Experimental Example C: Upconversion Emission Signal Analysis with or without Retroreflection Particles To investigate the signal detection of the retroreflection-based upconversion emission observation optical system, the upconversion emission signal based on the presence or absence of the retroreflection particles was analyzed.

Figure 8:
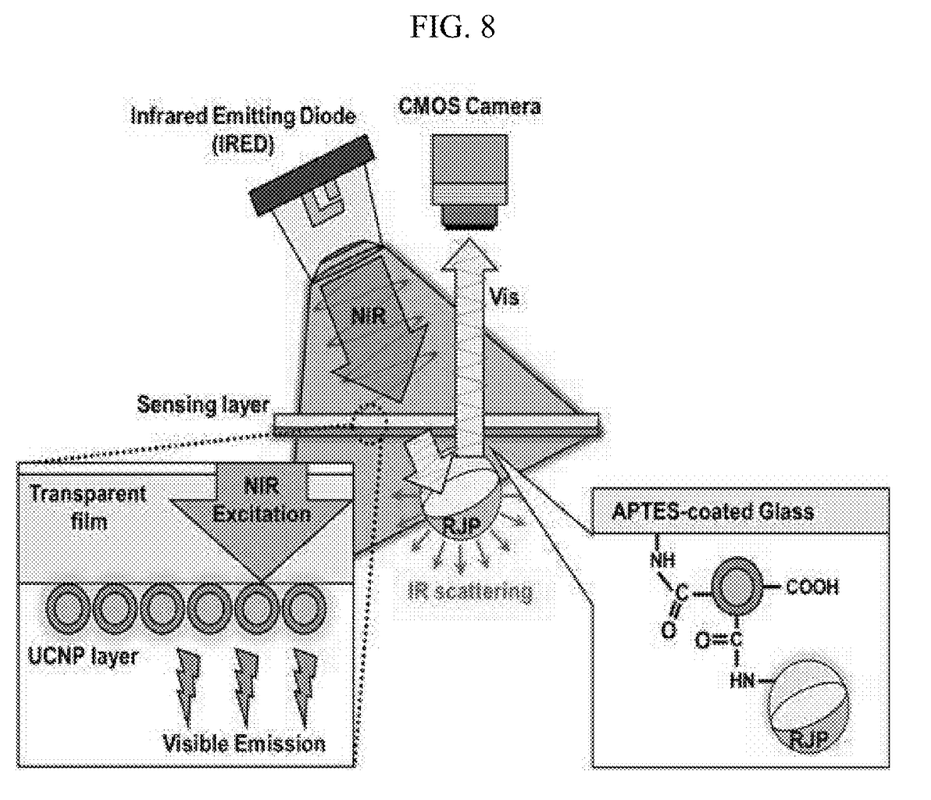
FIG. 8 is a diagram showing a schematic diagram of obtaining an upconversion emission signal according to reaction of the retroreflection particles and the signal converter according to Experimental Example C of the present disclosure.

FIG. 8 is a diagram showing a schematic diagram of obtaining an upconversion emission signal according to the reaction of the retroreflection particles and the signal converter according to Experimental Example C of the present disclosure.

Referring to FIG. 8, when the retroreflection particles are bonded to the signal converter fixed on the transparent substrate, the retroreflection particles were immobilized to the signal converter via covalent bonds based on two bonds: an amide bond from the amine group modified on the transparent substrate to the carboxyl group of the upconversion nanoparticles, and an amide bond from carboxyl groups of the upconversion nanoparticles to amine groups modified on the surface of retroreflection particles. Then, whether the upconversion emission signal was retroflected identified.

For a case when the retroreflection particles are coupled to the signal converter fixed to the transparent substrate and a case when the retroreflection particles are not coupled to the signal converter, whether the upconversion emission signal generated when irradiating a 980 nm laser light on the upconversion particles was reflected from the retroreflection particles and then was observed by the CMOS camera was identified. The results are shown in FIGS. 9A and 9B.

Figure 9A:
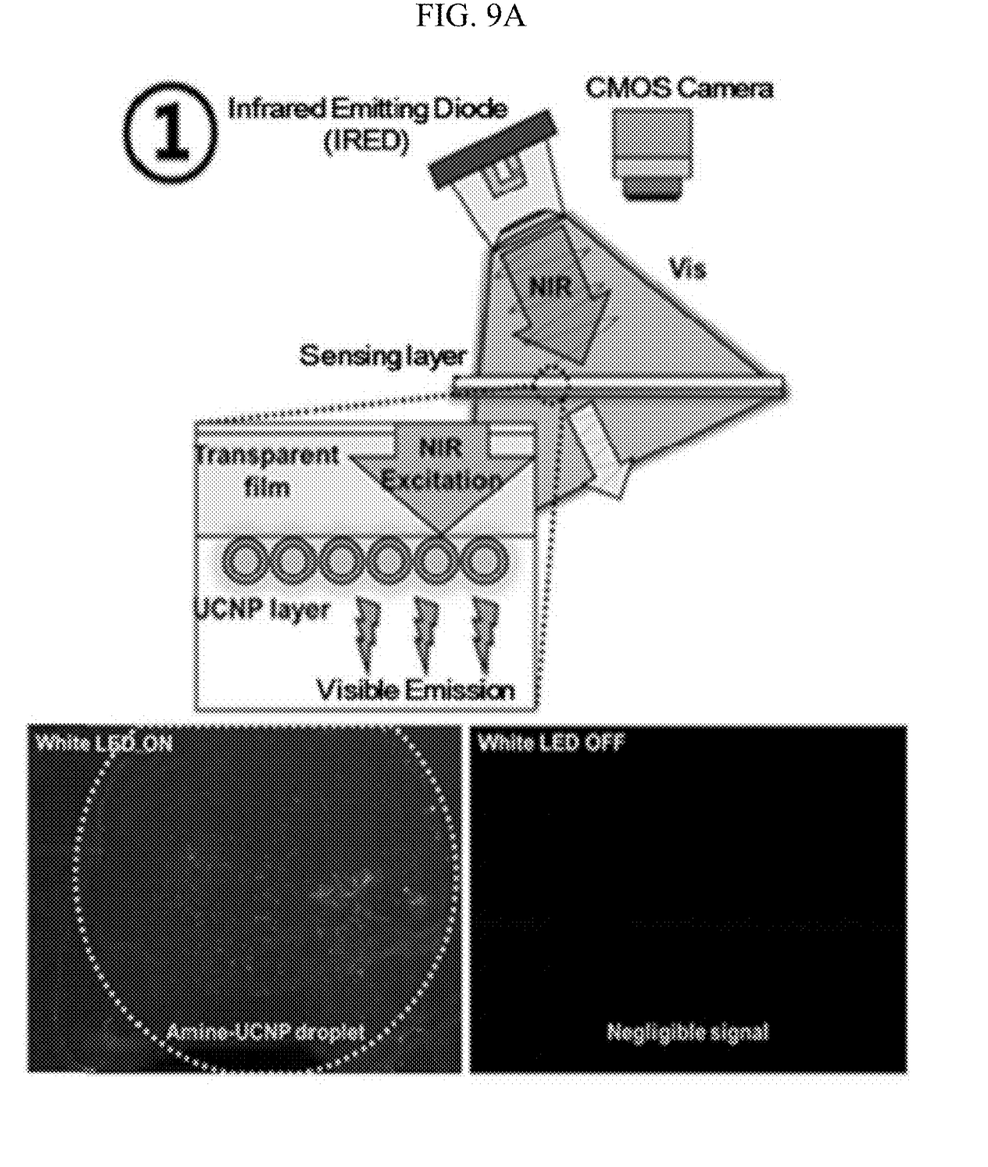
FIGS. 9A and 9B are diagrams showing results of upconversion emission signal analysis based on presence or absence of retroreflection particles in Experimental Example C of the present disclosure. ① in FIG. 9A is an image showing the analysis result of the upconversion emission signal under absence of the retroreflection particles. ② in FIG. 9B is an image showing the analysis result of the upconversion emission signal under presence of the retroreflection particles.
Figure 9B:
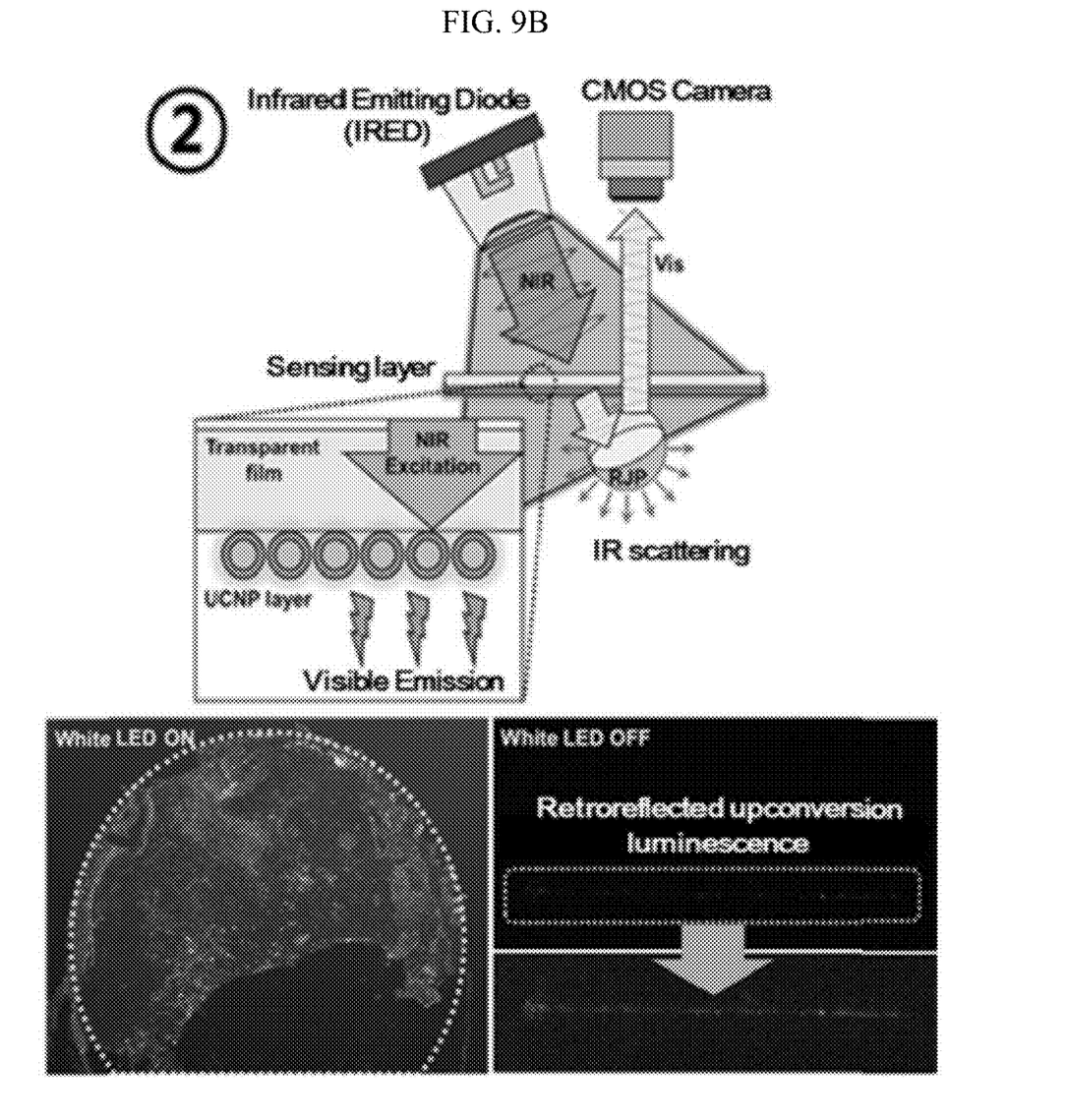

Referring to ① in FIG. 9A, referring to the observation result of the retroreflection signal of the upconversion nanoparticles layer for the case when no retroreflection particles are not coupled to the signal converter, yellow-green light emission could be identified with the naked eye when irradiating the laser light thereto. However, no emission was observed on the image as obtained by the CMOS camera. On the other hand, referring to ② in FIG. 9B, when the retroreflection particles are bound to the upconversion nanoparticles, the upconversion emission may be identified on the image obtained using the CMOS camera. Thus, it may be seen that when only the upconversion nanoparticles are used, an intensity of light emitted from the upconversion nanoparticles is weak such that the light may not reach the image sensor of the retroreflection optical system. Further, it may be seen that when using the upconversion nanoparticles coupled to the retroreflection particles, the light emitted from the upconversion nanoparticles is retroreflected from the retroreflection particles to provide a sufficiently strong signal such that the signal may be measured by the image sensor.

Experimental Example D: Operation Verification of Optical Bio-Sensing Device Using Laser Scanning Based on the contents derived from Experimental Example C that the upconversion emission signal is enhanced due to the combination of the retroreflection particles and the signal converter having the upconversion nanoparticles, and thus the signal is detected by the CMOS camera of the retroreflection optical system, it was determined that the device according to the present disclosure could be used for a biosensing platform. However, an irradiation area of the near-infrared laser light as the excitation light was evaluated to be somewhat narrow. To solve this problem, the upconversion emission signals as observed while moving a predefined laser irradiation area using a time-lapse imaging technique based on a scan of the laser light were collected. Thus, possibility of a large area scan that could be performed based on the present disclosure was identified. The upconversion emission signal from the retroreflection particles appearing in a section scanned by the laser during the image processing process using the time-lapse imaging technique was expressed as a single image. The results are shown in FIG. 10.

Figure 10:
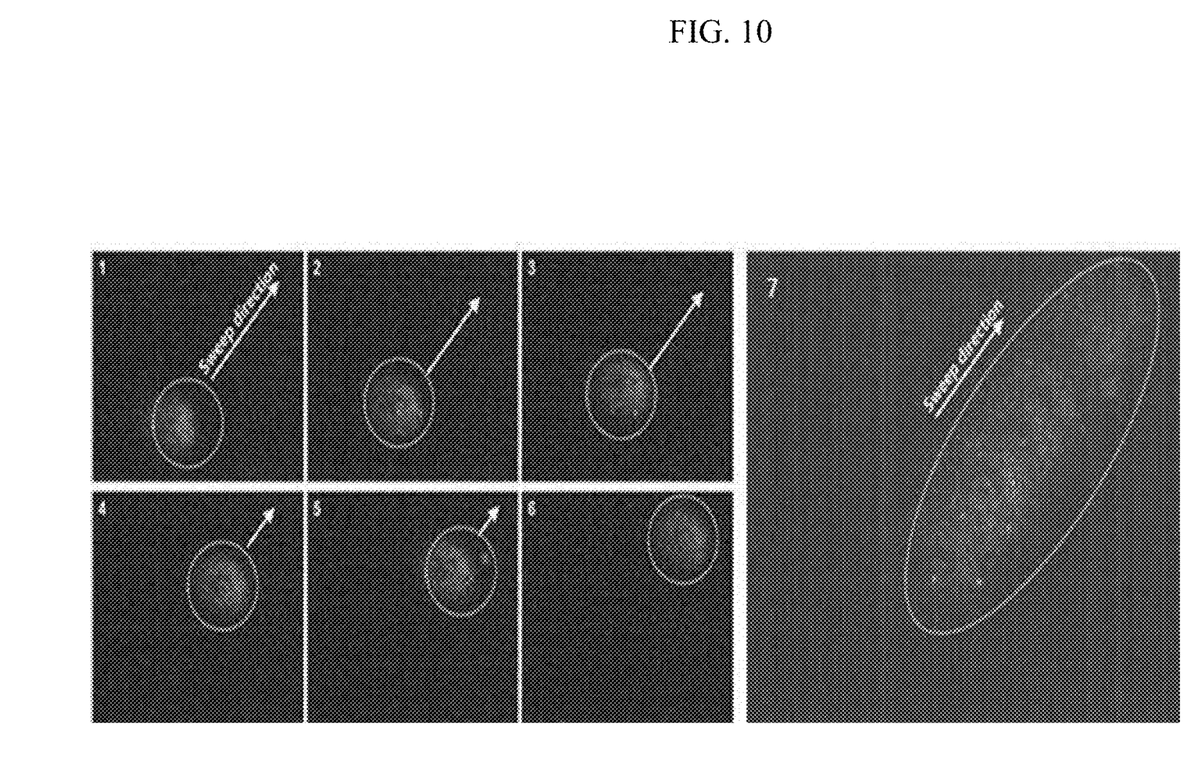
FIG. 10 is a diagram to analyze operation verification of the optical bio-sensing device using laser scanning of Experimental Example D of the present disclosure. Images 1 to 6 in FIG. 10 show images obtained by taking the upconversion emission signal using a time-lapse technique while moving an irradiation area of (near-)infrared laser in a single direction. 7 of FIG. 10 is a diagram showing one image by collecting the images 1 to 6 and performing image calculation.

Referring to FIG. 10, it may be seen that signal emitted from the upconversion nanoparticles and retroreflected from the retroreflection particles is observed in portions marked as an ellipses in 1 to 6 of FIG. 10. Each bright dot may be identified in 7 of FIG. 10 as a collection of the images into a single image. This dot represents the signal emitted from upconversion nanoparticles and retroflected from the retroreflection particles. Therefore, it may be seen that the emission signal may be observed on a surface of a large-area transparent substrate using a emission signal detection method based on infrared laser scanning.

Experimental Example E: Measurement Method of Upconversion Emission Signal Via Aggregation Reaction of Upconversion Nanoparticles and Retroreflection Particles In the analysis method using the optical bio-sensing device according to the present disclosure, in order to test that analysis is possible via the coupling between the signal converter and the retroreflection particles while the signal converter is not fixed to the transparent substrate, an aggregation reaction between the upconversion nanoparticles of the signal converter not fixed to the transparent substrate and the retroreflection particles was induced via an antigen-antibody reaction. Whether the upconversion emission signal reflected from the retroreflection particles was observed was identified based on the scan of the laser light and using the CMOS camera. The results are shown in FIG. 11.

Figure 11:
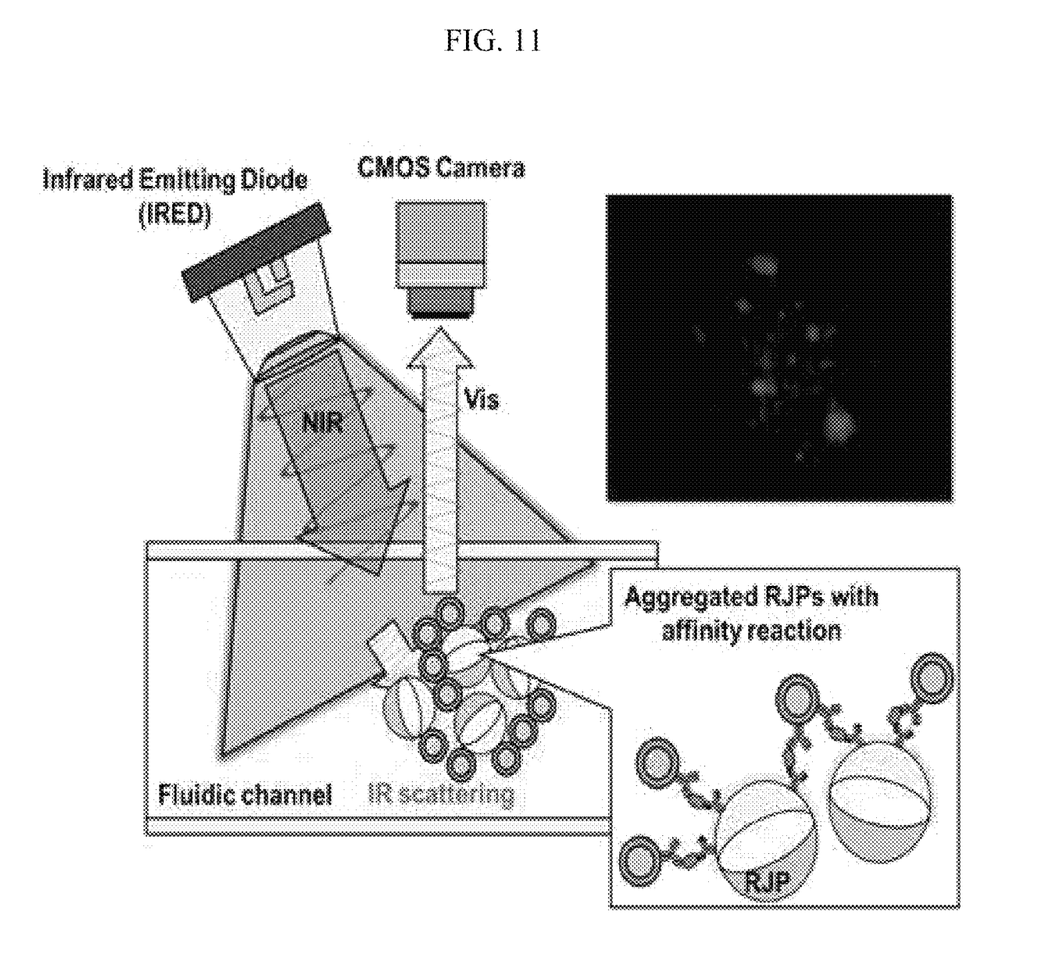
FIG. 11 is a schematic diagram of an upconversion emission signal measurement via aggregation of upconversion nanoparticles and retroreflection particles in Experimental Example E, and a diagram showing an image obtained via a CMOS camera.

Referring to FIG. 11, it may be seen that the emission signal appears in a form of a bulk. Thus, it may be seen that in the optical bio-sensing device according to the present disclosure, while the signal converter is not fixed to the transparent substrate, the analysis is possible only via the coupling between the signal converter and the retroreflection particles. This may be used in biosensing techniques that require an aggregation reaction.

It will be understood that although the above disclosure has been described with reference to the preferred embodiment of the present disclosure, those skilled in the art may achieve modifications and changes thereto within a range that does not deviate from the spirit and region of the present disclosure as described in the following claims.

What is claimed is:

1. An optical bio-sensing device for bio-material analysis using upconversion nanoparticles, the optical bio-sensing device comprising:
a transparent substrate covering a top of a space accommodating therein a sample containing a target bio-material;
a signal converter fixed to the transparent substrate, and including the upconversion nanoparticles for receiving incident light and emitting converted light of a wavelength shorter than a wavelength of the incident light;
a signal reflector including retroreflection particles bindable to the signal converter via the target bio-material, wherein the retroreflection particles retroreflect the converted light;
a light source for irradiating the incident light to the signal converter; and
a light receiver for receiving light retroreflected from the signal reflector,
wherein the target bio-material is in contact with the upconversion nanoparticles of the signal converter and is bonded to the upconversion nanoparticles of the signal converter, and
where the target bio-material is in contact with the retroreflection particles of the signal reflector and is bonded to the retroreflection particles of the signal reflector.

2. The optical bio-sensing device for bio-material analysis of claim 1, wherein the signal converter includes the upconversion nanoparticles chemically binding to a bottom face of the transparent substrate.

3. The optical bio-sensing device for bio-material analysis of claim 1, wherein the signal converter includes a transparent polymer film formed on a bottom face of the transparent substrate, wherein the upconversion nanoparticles are dispersed in the transparent polymer film.

4. The optical bio-sensing device for bio-material analysis of claim 1, wherein each of the upconversion nanoparticles is made of a compound represented by a following Chemical Formula 1:

$$NaYREF_4 \qquad \text{<Chemical Formula 1>}$$

wherein in the Chemical Formula 1, RE represents one selected from a group consisting of Yb, Er, Tm, Gd, Mn, Lu, Ce and Nd.

5. The optical bio-sensing device for bio-material analysis of claim 1, wherein each of the retroreflection particles includes a first bio-recognition material capable of selectively binding to the target bio-material, wherein the signal converter includes a second bio-recognition material capable of selectively binding to the target bio-material.

6. The optical bio-sensing device for bio-material analysis of claim 1, wherein when the incident light having a wavelength of an infrared region is irradiated onto the upconversion nanoparticles, the upconversion nanoparticles convert the incident light to the converted light having a wavelength of a visible region, and emit the converted light, wherein the retroreflection particles retroreflect the converted light.

7. The optical bio-sensing device for bio-material analysis of claim 1, wherein a size of each of the retroreflection particles is smaller than a wavelength of the incident light and is larger than a wavelength of the converted light.

8. A method for quantitative analysis of a bio-material using the optical bio-sensing device of claim 1, the method comprising:
a first step of reacting the retroreflection particles with a detection target solution containing the target bio-material;
a second step of selectively binding the signal reflector including the retroreflection particles bonded to the target bio-material to the signal converter;
a third step of irradiating the incident light of an infrared wavelength region to the signal converter;
a fourth step of retroreflecting the converted light of a visible wavelength region from the signal converter using the retroreflection particles; and
a fifth step of generating and analyzing an image of the retroreflected light.

9. The method of claim 8, wherein a size of each of the retroreflection particles is smaller than a wavelength of the incident light and is larger than a wavelength of the converted light, such that the incident light is scattered from the retroreflection particles, and the converted light is retroreflected from the retroreflection particles.

10. The method of claim 8, wherein the method further comprises, after the second step and before the third step, removing the signal reflector that does not bind to the signal converter.

11. The method of claim 8, wherein the fifth step includes counting a number of signals of the signal reflector based on the generated image, and quantitatively analyzing a concentration of the target material, based on the counted number.

* * * * *